(12) United States Patent
Murahashi et al.

(10) Patent No.: US 6,482,989 B2
(45) Date of Patent: Nov. 19, 2002

(54) METHOD FOR OXIDIZING ALKANES AND CYCLOALKANES WITH ALDEHYDES IN THE PRESENCE OF COPPER-BASED CATALYSTS AND NITROGEN-CONTAINING COMPOUNDS

(75) Inventors: Shun-ichi Murahashi, Ikeda (JP); Naruyoshi Komiya, Ashiya (JP); Yukiko Hayashi, Toyonaka (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 09/906,752

(22) Filed: Jul. 18, 2001

(65) Prior Publication Data

US 2002/0045778 A1 Apr. 18, 2002

(30) Foreign Application Priority Data

Jul. 19, 2000 (JP) .......................................... 2000-218512

(51) Int. Cl.$^7$ .......................... C07C 45/28; C07C 37/08; C07C 27/10
(52) U.S. Cl. ...................... 568/315; 568/322; 568/344; 568/357; 568/389; 568/392; 568/741; 568/771; 568/802; 568/910
(58) Field of Search ................................. 568/315, 321, 568/322, 344, 357, 360, 389, 392, 405, 741, 771, 802, 911, 952

(56) References Cited

U.S. PATENT DOCUMENTS 5,426,237 A * 6/1995 Murahashi et al.

FOREIGN PATENT DOCUMENTS

JP 03-081241 4/1991

OTHER PUBLICATIONS

Herbert O. House. Modern Synthetic Reactions, $2^{nd}$ Ed., 1972. p 270, 310.*
Naruyoshi Komiya, et al. "Aerobic oxidation of alkanes and alkenes in the presence fo aldehydes catalyzed by copper salts and cooper–crown ether[1]," 117 Journal of Molecular Catalysis a: Chemical 21–37 (1997).

* cited by examiner

*Primary Examiner*—Sreeni Padmanabhan
*Assistant Examiner*—Sikarl Witherspoon
(74) *Attorney, Agent, or Firm*—Burns, Doane, Swecker & Mathis, LLP

(57) ABSTRACT

A method for oxidizing an alkane, comprising the step of oxidizing said alkane with oxygen in the presence of an aldehyde, a copper-based catalyst and a nitrogen-containing compound. This method may be used to convert alkanes to corresponding alcohols and ketone having pharmaceutical activities, etc.

21 Claims, No Drawings

METHOD FOR OXIDIZING ALKANES AND CYCLOALKANES WITH ALDEHYDES IN THE PRESENCE OF COPPER-BASED CATALYSTS AND NITROGEN-CONTAINING COMPOUNDS

BACKGROUND OF THE INVENTION

1. Filed of the Invention

The present invention relates to a method for oxidizing alkanes with oxygen in catalytically oxidizing reactions. In this specification, the alkanes include cycloalkanes In the present invention, the alkanes and the cycloalkanes include substituted alkanes and substituted cycloalkanes, respectively. Further, the cycloalkanes include condensed rings in which an aromatic ring is condensed with a cycloalkane ring at an ortho position.

2. Related Art Statement

In the fields of the organic chemistry and the industrial chemistry, the necessity for methods of introducing oxygen functional groups in alkanes has been increasing in recent years, and earlier development of effective oxygen-oxidizing reactions has been demanded.

Alcohols and ketones obtained by oxidizing alkanes can be used as building blocks and starting materials for medicines, chemical products and polymers as well as various functional materials.

Heretofore, an automatic oxidizing method which undergoes a free radical reaction in the presence of a cobalt-based catalyst is used as an industrial method for oxidizing alkanes with oxygen. However, such an automatic oxidizing method required high temperature and high pressure conditions to realize a sufficient oxidation speed, and further needed to suppress the conversion rate at a low level to selectively obtain intended alcohol and ketone. In order to solve such problems, an oxygen-oxidizing method which is based on a new principle with use of a gentle condition of an oxygen pressure of 1 atm has been strongly demanded.

Under the circumstances, various examinations have been effected with respect to the oxidation of hydrocarbons with oxygen with use of the gentle condition of 1 atm. For example, one equivalent or more reducing agent is used for oxidizing a hydrocarbon with oxygen at 1 atm. As the reducing agent, zinc (J. Chem. Soc., Perkin. Trans. 1 1986, 947; J. C hem. Soc., Chem. Commun. 1991, 102; New J. Chem. 16, 621 (1992)), hydrazine (J. Am. Chem. Soc. 112, 879 (1990)), hydrogen (J. Am. Chem. Soc. 103, 7371 (1981); J. Am. Chem. Soc. 109, 2837 (1987); J. Chem. Soc., Chem. Commun. 1992, 1446), hydrogen sulfide (Chem. commun. 1997, 557), ascorbic acid salt (Tetrahedron 40, 4297 (1984)), hydroquinone (Chem. Lett. 1991, 1819), etc. were proposed. Each of the above reacting systems has a problem in that the yield of the product and the turnover number of the catalyst are low.

On the other hand, the present inventors discovered a method of oxygen-oxidizing alkanes with use of aldehydes in the presence of a copper/crown ether catalyst or a copper/crown ether/inorganic salt catalyst (JP-A 6-263,664 and JP-A 11-255,682). Although this method enables the alkane to be oxidized with use of oxygen at 1 atm, it has been demanded to construct an inexpensive catalyst system having further improved catalytic activity (turnover number) and substituting for crown ethers.

SUMMARY OF THE INVENTION

The present inventors made further investigations to improve the catalytic activity with due consideration of economy, and discovered that the catalytic activity is greatly improved by coordinating a nitrogen-containing compound such as a nitrile into a copper catalyst. The inventors reached the present invention based on this discovery. That is, the present invention is to provide a method for oxidizing an alkane and a cycloalkane with oxygen in the presence of an aldehyde, a copper catalyst and a nitrogen-containing material as an auxiliary ligand. In the present claims, the alkane includes the cycloalkane.

DETAILED DESCRIPTION OF THE INVENTION

In the following, the present invention will be described in more detail. (1) Alkanes Specific examples of the alkanes and the cycloalkanes to be used in the oxidizing method of the present invention are given below.

(1-1) Alkanes

As the alkanes, represented by a general formula $C_nH_{2n+2}$ (n=1 to 30), n-pentane, n-hexane, n-heptane, n-octane, n-nonane, n-decane, n-undecane, n-dodecane, etc. may be recited, for example. In the present invention, the alkane includes the substituted alkane represented by a general formula $C_nH_{2n+1}R$ in which n=1 to 30, R denotes a carboxylic group, an ester group, a halogen group, a nitro group, a methoxy group, or an alkyl group or an aromatic group which may be substituted by a carboxylic group, an ester group, a halogen group, a nitro group or a methoxy group are included. As representative examples of the alkanes, mention may be made of toluene, p-xylene, m-xylene, o-xylene, 4-methoxytoluene, 3-methoxytoluene, 2-methoxytoluene, 4-chlorotoluene, 3-chlorotoluene, 2-chlorotoluene, ethylbenzene, diphenylmethane, 4-nitrotoluene, decanoic acid, methyl decanate.

(1-2) Cycloalkanes

The cycloalkane, which may be represented by a general formula $C_nH_{2n}$ (n=5 to 30), and mention may be made of cyclohexane, cyclopentane, cyclooctane, cycloheptane, cyclododecane, etc. In the present invention, the cycloalkane may include a cycloalkane represented by a general formula $C_nH_{2n-1}R$ in which n=5 to 30, R denotes a carboxylic group, an ester group, a halogen group, a nitro group, a methoxy group, or an alkyl group or an aromatic group which may be substituted by a carboxylic group, an ester group, a halogen group, a nitro group or a methoxy group. As examples of the cycloalkanes, mention may be made of methylcyclohexane, adamantane, cis-decalin, trans-decalin, cyclohexane carboxylic acid, cyclohexane carboxylic acid, methylchlorocyclohexane, nitrocyclohexane, etc. The cycloalkanes include a condensed ring in which an aromatic ring and a cycloalkane ring are condensed at an ortho position. As examples thereof, indane, 5, 6-dimethoxyindane, tetralin, fluorene, etc. may be recited.

(2) Copper-based Catalysts

As copper-based catalysts to be used in the present invention, conventionally known inorganic copper salts may be employed. For example, $Cu(OAc)_2\text{-}nH_2O$, $Cu(OAc)$, $Cu(OCOCF_3)_2$, $CuCN$, $CuCl$, $CuCl_2\text{-}nH_2O$, $CuBr$, $CuBr_2$, $CuSO_4\text{-}nH_2O$, $Cu(NO_3)_2\text{-}nH_2O$, $Cu(ClO_4)_2$, $Cu(OCH_3)_2$, $Cu(PO_4)_2\text{-}nH_2O$, $CuO$, $Cu_2O$, $Cu(acac)_2$, $Cu(OH)_2$, Cu powder, etc. in which n is an integer of 0 to 6. In addition, copper coordination compounds which is preliminarily replaced by a nitrogen-series ligand, and peroxo crosslinked binuclear copper complexes easily formed therefrom in the presence of oxygen may be employed. For example, mention may be made of X, X ($C_5H_5N$: pyridine), X (bpy=2, 2'-bipyridine), $X_2$ ($C_3H_4N_2$: imidazole), $X_2$ (phen=1, 10-phenanthroline), $X_2$ ($C_{14}H_{32}N_4$=1, 4, 8, 11-tetramethyl-1, 4, 8, 11-tetraazacyclotetradecane), X (tmpa =tris(2-pyridylmethyl)amine), X, $X_2$, X in which X, X are Cl, $NO_3$, $ClO_4$, $PF_6$, $BF_4$ or the like. Among them, $Cu(OAc)_2$ which is easily available and handled and has high reactivity is preferably used. The use amount of the copper-based catalyst is not particularly limited, but it is ordinarily in a range of 0.000001 to 200 mol %, preferably in a range of 0.00001 to 5 mol % relative to a substrate.

(3) Aldehydes

As the aldehydes to be used in the present invention, aliphatic aldehydes and aromatic aldehydes may be employed. More specifically, mention may be made of aliphatic aldehydes such as acetaldehyde, propionaldehyde, n-butylaldehyde, isobutylaldehyde, n-valeraldehyde, isovaleraldehyde, pivalaldehyde, n-hexylaldehyde, n-heptylaldehyde, n-octylaldehyde, n-nonylaldehyde, n-decylaldehyde, etc., substituted or non-substituted aromatic aldehydes such as benzaldehyde, p-chlorobenzaldehyde, m-chlorobenzaldehyde, m-cyanobenzaldehyde, p-tolualdehyde, p-methoxybenzaldehyde, etc, and mixtures of the above aldehydes. Among them, acetaldehyde which is easily industrially available is preferably employed from the standpoint of reactivity and economy. The use amount of the aldehyde is not particularly limited, but it is ordinarily in a range of 0.1 to 1000 mol %, preferably in a range of 1 to 400 mol % relative to the substrate.

(4) Nitrogen-containing compounds

The nitrogen-containing compounds to be used in the present invention may be nitrites, aromatic amines and tertiary amines. As the nitrites, conventionally known nitrites may be used, irrespective of aliphatic nitrites or aromatic nitrites. As specific examples of the aliphatic nitrites, mention may be made of acetonitrile, propionitrile, butylonitrile, isobutylonitrile, valeronitrile, isovaleronitrile, trimethylacetonitrile, hexane nitrile, 4-methylvaleronitrile, heptane nitrile, octane nitrile, undecane nitrile, decane nitrile, stearonitrile, cyclohexane carbonitrile, cyclopentane carbonitrile, etc. As aliphatic dinitriles, mention may be made of malononitrile, succinonitrile, glutaronitrile, adiponitrile, pimelonitrile, suberonitrile, azelanitrile, etc. As the aromatic nitrites, benzonitrile, o-, m-, p-phthalonitriles, etc. may be recited. As specific examples of the aromatic amines and the tertiary amines, mention may be made of non-substituted or substituted amines or derivatives such as pyridine, 2, 2 bipyridine, 2, 2 biquinoline (biquinoline), 2, 2:6 2 terpyridine (terpyridine), imidazole, pyrazole, 1, 10-phenanthroline, 1, 4, 8, 11-tetramethyl-1, 4, 8, 11-tetraazacyclotetradecane, tris(2-pyridylmethyl)amine, etc. Among them, acetonitrile is preferably employed from the standpoint of reactivity and economy. The amount of the nitrile, the aromatic amine or the tertiary amine is not particularly limited, but it is ordinarily in a range of 0.000001 to 50 equivalents relative to the substrate. The amount of the nitrile is preferably in a range of 1 to 2 equivalents relative to the substrate.

(5) Reacting conditions (5-1) Solvents

With respect to the solvent to be used in the present reaction, a hydrocarbon (for example, cyclohexane) as a substrate may be used as functioning as both a substrate and a solvent. Further, another solvent may be used. As the solvent, use may be made of halogenated hydrocarbons (methylene chloride, chloroform, etc.), ketones (acetone, etc.), esters (ethyl acetate, etc.), carboxylic acids (acetic acid, etc.), aromatic hydrocarbons (benzene, chlorobenzene, etc.), etc. They may be used singly or in a mixed state of two or more of them.

(5-2) Reacting temperature

The reacting temperature is ordinarily in a range of 0° C. to 150° C., preferably in a range of 25° C. to 80° C. Although the reaction proceeds when the reacting temperature is room temperature such as 20° C., about 10 to 100 times as much as the catalyst is necessary, and the reaction time becomes longer in some cases.

(5-3) Other treatments

After the reaction solution is treated with an aqueous solution of sodium hydrogensulfite, the catalyst can be removed from an alcohol or a ketone produced corresponding to the alkane or the cycloalkane in the present reaction by a treatment such as washing with water. The alcohol or ketone can be easily separated from the reaction mixture by an operation such as distillation, if necessary.

(5-4) Oxidation reaction

A method for carrying out the oxygen-oxidizing reaction will be explained.

As oxygen used in the present reaction, any one of (a) oxygen gas, (b) air (oxygen 20%, nitrogen 78%, carbon dioxide 1%, etc.), (c) a mixture of oxygen gas and an inert gas such as nitrogen may be used. The pressure of the gas may be a reduced pressure or a pressurized pressure, but the oxygen pressure may be 1 atm.

It is preferable that the reaction is effected in an experiment at around room temperature in the state that a reacting container is attached with an oxygen-filled balloon for supplying oxygen at 1 atm.

In a high-temperature experiment at 40° C. or more, an autoclave made of Hastelloy is preferably used. The reaction in the experiment is preferably effected such that the container is first replaced with nitrogen at 8 atm, and the autoclave is connected to an apparatus to which oxygen is always fed at 1 atm starting from the reaction start and during the reaction.

Further, the aldehyde to be used in the reaction is purified, if necessary (For example, aldehyde is used as being distilled).

(5-5)

The method of oxidizing the alkanes and the cycloalkanes according to the present invention is considered as follows. For example, when acetoaldehyde and a divalent copper catalyst are taken as an example, acetoaldehyde generates acyl radicals in the presence of the divalent copper catalyst, which produces a peracetic acid with oxygen through an automatic oxidation process. At this time, the divalent copper is reduced to monovalent copper. The resulting monovalent copper reacts with peracetic acid to form a trivalent copper active species, which extracts a hydrogen atom from the alkane. Following this, an alcohol is produced through recoupling of a hydroxyl ligand, and monovalent copper is reproduced. The alcohol is oxidized in a similar way.

EXAMPLES

Although the present invention will be concretely explained with reference to examples, these examples never limit the invention at all. First, examples in which alkanes or cycloalkanes were oxidized at 70° C. are shown.

Example 1

Oxidation of Cyclohexane—(1)~(2)

1-(1) When a mixed solvent (15 ml) of acetonitrile/dichloromethane was used:

After cyclohexane (120 mmol), $Cu(OAc)_2$ ($7.5 \times 10^{-5}$ mmol), acetaldehyde (3 mmol), acetonitrile (9 ml) and dichloroethane (6 ml) were charged into a glass container in an autoclave made of Hastelloy, the container was pressurized with nitrogen at 8 atm. Then, oxygen at 1 atm was introduced (totally 9 atm), and the mixture was stirred at 70° C. for 24 hours. After the reaction mixture was cooled to room temperature, the interior pressure was returned to 1 atm. The reaction mixture was analyzed with a gas chromatography, which revealed that the yield of cyclohexanol was 41% (relative to 1 equivalent of acetaldehyde), that of cyclohexanone was 54% (relative to 2 equivalents of acetaldehyde), and the turnover number of the catalyst was 27000.

1-(2) When a small amount of acetonitrile solvent (1.5 ml) was used:

After cyclohexane (120 mmol), $Cu(OAc)_2$ ($7.5 \times 10^{-5}$ mmol), acetaldehyde (12.0 mmol), and acetonitrile (1.5 ml) were charged into a glass container in the autoclave made of Hastelloy, the container was pressurized with nitrogen at 8 atm. Then, oxygen at 1 atm was introduced (totally 9 atm), and the mixture was stirred at 70° C. for 24 hours. After the reaction mixture was cooled to room temperature, the interior pressure was returned to 1 atm. The reaction mixture was analyzed with the gas chromatography, which revealed that the yield of cyclohexanol was 13% (relative to 1 equivalent of acetaldehyde), that of cyclohexanone was 28% (relative to 2 equivalents of acetaldehyde), and the turnover number of the catalyst was 42000.

Example 2

Oxidation of Cyclooctane

After cyclooctane (120 mmol), $Cu(OAc)_2$ ($7.5 \times 10^{-5}$ mmol), acetaldehyde (12.0 mmol), and acetonitrile (6 ml) were charged into a glass container in the autoclave made of Hastelloy, the container was pressurized with nitrogen at 8 atm. Then, oxygen at 1 atm was introduced (totally 9 atm), and the mixture was stirred at 70° C. for 24 hours. After the reaction mixture was cooled to room temperature, the interior pressure was returned to 1 atm. The reaction mixture was analyzed with the gas chromatography, which revealed that the yield of cyclooctanol was 3% (relative to 1 equivalent of acetaldehyde), that of cyclooctanone was 19% (relative to 2 equivalents of acetaldehyde), and the turnover number of the catalyst was 21000.

Example 3

Oxidation of n-hexane

After n-hexane (120 mmol), $Cu(OAc)_2$ ($3.0 \times 10^{-5}$ mmol), acetaldehyde (3.0 mmol), acetonitrile (9.0 ml) and dichloromethane (6 ml) were charged into a glass container in the autoclave made of Hastelloy, the container was pressurized with nitrogen at 8 atm. Then, oxygen at 1 atm was introduced (totally 9 atm), and the mixture was stirred at 70° C. for 24 hours. After the reaction mixture was cooled to room temperature, the interior pressure was returned to 1 atm. The reaction mixture was analyzed with the gas chromatography, which revealed that the yield of 2-hexanol and 3-hexanol was 6% (44:56) (relative to 1 equivalent of acetaldehyde), that of 2-hexanone and 3-hexanone was 25% (50:50) (relative to 2 equivalents of acetaldehyde), and the turnover number of the catalyst was 7200.

Example 4

Oxidation of cyclohexane—(1)~(7)

4-(1) $Cu(OAc)_2$/acetaldehyde/acetonitrile

After cyclohexane (40 mmol), $Cu(OAc)_2$ ($2.5 \times 10^{-3}$ mmol), acetaldehyde (4.0 mmol), acetonitrile (3 ml) and dichloromethane (2 ml) were charged into a 25-ml eggplant-type flask, and an oxygen balloon was attached to the flask for supplying oxygen at 1 atm. Then, the mixture was stirred at 25° C. for 48 hours. The reaction mixture was analyzed with the gas chromatography, which revealed that the yield of cyclohexanol was 9% (relative to 1 equivalent of acetaldehyde), that of cyclohexanone was 33% (relative to 2 equivalents of acetaldehyde), and the turnover number of the catalyst was 436.

4-(2) $Cu(OAc)$/acetaldehyde/acetonitrile

After cyclohexane (40 mmol), $Cu(OAc)$ ($2.5 \times 10^{-3}$ mmol), acetaldehyde (4.0 mmol), acetonitrile (3 ml) and dichloromethane (2 ml) were charged into a 25-ml eggplant-type flask, and an oxygen balloon was attached to the flask for supplying oxygen at 1 atm. Then, the mixture was stirred at 25° C. for 48 hours. The reaction mixture was analyzed with the gas chromatography, which revealed that the yield of cyclohexanol was 10% (relative to 1 equivalent of acetaldehyde), that of cyclohexanone was 34% (relative to 2 equivalents of acetaldehyde), and the turnover number of the catalyst was 449.

4-(3) Cu powder/acetaldehyde/acetonitrile

After cyclohexane (80 mmol), Cu powder ($2.0 \times 10^{-2}$ mmol), acetaldehyde (8.0 mmol), acetonitrile (5 ml) and dichloromethane (5 ml) were charged into a 50-ml eggplant-type flask, and an oxygen balloon was attached to the flask for supplying oxygen at 1 atm. Then, the mixture was stirred at 25° C. for 24 hours. The reaction mixture was analyzed with the gas chromatography, which revealed that the yield of cyclohexanol was 10% (relative to 1 equivalent of acetaldehyde), that of cyclohexanone was 34% (relative to 2 equivalents of acetaldehyde), and the turnover number of the catalyst was 110.

4-(5) $Cu(OAc)$/acetaldehyde/pyridine

After cyclohexane (40 mmol), $Cu(OAc)_2$ ($1.0 \times 10^{-2}$ mmol), acetaldehyde (4.0 mmol), pyridine ($1.0 \times 10^{-2}$ ml) and dichloromethane (5 ml) were charged into a 25-ml eggplant-type flask, and an oxygen balloon was attached to the flask for supplying oxygen at 1 atm. Then, the mixture was stirred at 25° C. for 36 hours. The reaction mixture was analyzed with the gas chromatography, which revealed that the yield of cyclohexanol was 9% (relative to 1 equivalent of acetaldehyde), that of cyclohexanone was 21% (relative to 2 equivalents of acetaldehyde), and the turnover number of the catalyst was 79.

4-(5) $Cu(OAc)_2$/acetaldehyde/glutaronitrile

After cyclohexane (80 mmol), $Cu(OAc)_2$ ($2.0 \times 10^{-2}$ mmol), acetaldehyde (8.0 mmol), glutaronitrile (5 ml) and dichloromethane (15 ml) were charged into a 25-ml eggplant-type flask, and an oxygen balloon was attached to the flask for supplying oxygen at 1 atm. Then, the mixture was stirred at 25° C. for 48 hours. The reaction mixture was analyzed with the gas chromatography, which revealed that the yield of cyclohexanol was 11% (relative to 1 equivalent of acetaldehyde), that of cyclohexanone was 27% (relative to 2 equivalents of acetaldehyde), and the turnover number of the catalyst was 98.

4-(6) $Cu(OAc)_2$/acetaldehyde/benzonitrile

After cyclohexane (40 mmol), $Cu(OAc)_2$ ($2.5 \times 10^{-3}$ mmol), acetaldehyde (4.0 mmol), benzonitrile (2.5 ml) and dichloromethane (2.5 ml) were charged into a 25-ml eggplant-type flask, and an oxygen balloon was attached to the flask for supplying oxygen at 1 atm. Then, the mixture was stirred at 25° C. for 48 hours. The reaction mixture was analyzed with the gas chromatography, which revealed that the yield of cyclohexanol was 9% (relative to 1 equivalent of acetaldehyde), that of cyclohexanone was 29% (relative to 2 equivalents of acetaldehyde), and the turnover number of the catalyst was 375.

4-(7) $CuCl_2$/benzoaldehyde/1, 4, 8, 11-tetramethyl-1, 4, 8, 11-tetraazacyclotetradecane After cyclohexane (80 mmol), $CuCl_2$ ($2.0 \times 10^{-2}$ mmol), benzaldehyde (8.0 mmol), 1, 4, 8, 11-tetramethyl-1, 4, 8, 11-tetraazacyclotetradecane ($2.0 \times 10^{-2}$ mmol) and dichloromethane (10 ml) were charged into a 50-ml eggplant-type flask, and an oxygen balloon was attached to the flask for supplying oxygen at 1 atm. Then, the mixture was stirred at 25° C. for 24 hours. The reaction mixture was analyzed with the gas chromatography, which revealed that the yield of cyclohexanol was 7% (relative to 1 equivalent of benzaldehyde), that of cyclohexanone was 10% (relative to 2 equivalents of benzaldehyde), and the turnover number of the catalyst was 51.

Example 5

Oxidation of Cyclooctane

After cyclohexane (40 mmol), $Cu(OAc)_2$ ($2.5 \times 10^{-3}$ mmol), acetaldehyde (4.0 mmol), acetonitrile (2 mmol) and dichloromethane (3 ml) were charged into a 25-ml eggplant-type flask, and an oxygen balloon was attached to the flask for supplying oxygen at 1 atm. Then, the mixture was stirred at 25° C. for 48 hours. The reaction mixture was analyzed with the gas chromatography, which revealed that the yield of cyclooctanol was 3% (relative to 1 equivalent of acetaldehyde), that of cyclooctanone was 33% (relative to 2 equivalents of acetaldehyde), and the turnover number of the catalyst was 310.

Example 6

Oxidation of n-hexane

After n-cyclohexane (40 mmol), $Cu(OAc)_2$ ($1.0 \times 10^{-3}$ mmol), acetaldehyde (4.0 mmol), acetonitrile (3 ml) and dichloromethane (2 ml) were charged into a 25-ml eggplant-type flask, and an oxygen balloon was attached to the flask for supplying oxygen at 1 atm. Then, the mixture was stirred at 25° C. for 24 hours. The reaction mixture was analyzed with the gas chromatography, which revealed that the yield of 2-hexanol and 3-hexanol was 2% (37:63) (relative to 1 equivalent of acetaldehyde), that of 2-hexanone and 3-hexanone was 2% (48:52) (relative to 2 equivalents of acetaldehyde), and the turnover number of the catalyst was 274.

Example 7

Oxidation of Ethylbenzene

After ethylbenzene (4.0 mmol), $Cu(OAc)_2$ ($2.5 \times 10^{-5}$ mmol), acetaldehyde (4.0 mmol), acetonitrile (3 ml) and dichloromethane (2 ml) were charged into a 25-ml eggplant-type flask, and an oxygen balloon was attached to the flask for supplying oxygen at 1 atm. Then, the mixture was stirred at 25° C. for 36 hours. The reaction mixture was analyzed with the gas chromatography, which revealed that the yield of 1-phenylethyl alcohol was 3% (relative to 1 equivalent of acetaldehyde), that of acetophenon was 25% (relative to 2 equivalents of acetaldehyde), and the turnover number of the catalyst was 24500.

Example 8

Oxidation of Indane

After indane (4.0 mmol), $Cu(OAc)_2$ ($2.5 \times 10^{-5}$ mmol), acetaldehyde (4.0 mmol), acetonitrile (3 ml) and dichloromethane (2 ml) were charged into a 25-ml eggplant-type flask, and an oxygen balloon was attached to the flask for supplying oxygen at 1 atm. Then, the mixture was stirred at 25° C. for 36 hours. The reaction mixture was analyzed with the gas chromatography, which revealed that the yield of 1-indanol was 8% (relative to 1 equivalent of acetaldehyde), that of 1 indanone was 53% (relative to 2 equivalents of acetaldehyde), and the turnover number of the catalyst was 54500.

Example 9

Oxidation of 1, 2, 3, 4-Tetrahydronaphthalene

After 1, 2, 3, 4-tetrahydronaphthalene (4.0 mmol), $Cu(OAc)_2$ ($2.5 \times 10^{-5}$ mmol), acetaldehyde (4.0 mmol), acetonitril (3 ml) and dichloromethane (2 ml) were charged into a 25-ml eggplant-type flask, and an oxygen balloon was attached to the flask for supplying oxygen at 1 atm. Then, the mixture was stirred at 25° C. for 36 hours. The reaction mixture was analyzed with the gas chromatography, which revealed that the yield of 1, 2, 3, 4-tetrahydro-1-naphthol was 12% (relative to 1 equivalent of acetaldehyde), that of x-tetralon was 67% (relative to 2 equivalents of acetaldehyde), and the turnover number of the catalyst was 72000.

Example 10

Oxidation of Adamantane

After adamantane (4.0 mmol), $Cu(OAc)_2$ ($1.0 \times 10^{-2}$ mmol), acetaldehyde (4.0 mmol), acetonitrile (2 ml) and dichloromethane (8 ml) were charged into a 25-ml eggplant-type flask, and an oxygen balloon was attached to the flask for supplying oxygen at 1 atm. Then, the mixture was stirred at 25° C. for 48 hours. The reaction mixture was analyzed with the gas chromatography, which revealed that the yield of 1-adamantanol was 16% (relative to 1 equivalent of acetaldehyde), that of 2-admantanol was 2% (relative to 1 equivalent of acetaldehyde), that of 2-adamantanone was 1% (relative to 2 equivalents of acetaldehyde), and the turnover number of the catalyst was 73.

According to the alkane and cycloalkane-oxidizing method in the present invention, the alcohol and the ketone can be produced at a high efficiency with a high turnover number through oxidation with oxygen using the copper salt as the catalyst and further in co-existence of the nitrogen-containing compound in the reaction system. That is, the present invention relates to the method for oxidizing the hydrocarbon with the copper-based catalyst characterized in that at least one kind of the nitrogen-containing compounds in the method of producing the alcohol and the ketone through the oxidation of the hydrocarbon with use of the aldehyde and the copper salt as the catalyst. According to the present invention, the yield of the product per the aldehyde and the turnover number of the catalyst can be increased, and the hydrocarbon such as the alkane and the alkylbenzene can be effectively oxidized. Thus, the invention has high utility.

What is claimed is:

1. A method for oxidizing an alkane, comprising the step of oxidizing said alkane with oxygen in the presence of an aldehyde, a copper-based catalyst and a nitrogen-containing compound wherein the nitrogen-containing compound forms a complex with the copper-based catalyst.

2. The oxidizing method set forth in claim 1, wherein said alkane is a hydrocarbon or a substituted hydrocarbon represented by a general formula $C_nH_{2n}$ or $C_nH_{2n-1}R$ in which n=1 to 30, R denotes a carboxylic group, an ester group, a halogen group, a nitro group, a methoxy group or an alkyl group or an aromatic group which may be substituted by a carboxylic group, an ester group, a halogen group, a nitro group or a methoxy group.

3. The oxidizing method set forth in claim 1, wherein said alkane is a cycloalkane, and the cycloalkane is a hydrocarbon or a substituted hydrocarbon represented by a general formula $C_nH_{2n}$ or $C_nH_{2n-1}R$ in which n=5 to 30, R denotes a carboxylic group, an ester group, a halogen group, a nitro group, a methoxy group or an alkyl group, an aromatic group-substituted alkyl group or an aromatic group which may be substituted by a carboxylic group, an ester group, a halogen group, a nitro group or a methoxy group.

4. The oxidizing method set forth in claim 3, wherein said copper-based catalyst is an inorganic copper catalyst or a copper coordination compound.

5. The oxidizing method set forth in claim 3, wherein said nitrogen-containing compound is a nitrile compound.

6. The oxidizing method set forth in claim 3, wherein said nitrogen-containing compound is an aromatic amine.

7. The oxidizing method set forth in claim 3, wherein said nitrogen-containing compound is a tertiary amine.

8. The oxidizing method set forth in claim 3, wherein said aldehyde is an aliphatic or aromatic aldehyde.

9. The oxidizing method set forth in claim 3, wherein said alkane is oxidized with oxygen to produce an alcohol and a ketone.

10. The oxidizing method set forth in claim 2, wherein said copper-based catalyst is an inorganic copper catalyst or a copper coordination compound.

11. The oxidizing method set forth in claim 2, wherein said nitrogen-containing compound is a nitrile compound.

12. The oxidizing method set forth in claim 2, wherein said nitrogen-containing compound is an aromatic amine.

13. The oxidizing method set forth in claim 2, wherein said nitrogen-containing compound is a tertiary amine.

14. The oxidizing method set forth in claim 2, wherein said aldehyde is an aliphatic or aromatic aldehyde.

15. The oxidizing method set forth in claim 2, wherein said alkane is oxidized with oxygen to produce an alcohol and a ketone.

16. The oxidizing method set forth in claim 1, wherein said copper-based catalyst is an inorganic copper catalyst or a copper coordination compound.

17. The oxidizing method set forth in claim 1, wherein said nitrogen-containing compound is a nitrile compound.

18. The oxidizing method set forth in claim 1, wherein said nitrogen-containing compound is an aromatic amine.

19. The oxidizing method set forth in claim 1, wherein said nitrogen-containing compound is a tertiary amine.

20. The oxidizing method set forth in claim 1, wherein said aldehyde is an aliphatic or aromatic aldehyde.

21. The oxidizing method set forth in claim 1, wherein said alkane is oxidized with oxygen to produce an alcohol and a ketone.

* * * * *